United States Patent
Honigsbaum et al.

(10) Patent No.: US 10,918,475 B2
(45) Date of Patent: Feb. 16, 2021

(54) SHRINK-WRAP ANCHORED AND SHRINK-WRAPPED ACTUATED ACCOMMODATIVE INTRAOCULAR LENSES AND METHODS FOR IMPLANTATION THEREOF

(71) Applicants: Richard F. Honigsbaum, Passaic, NJ (US); Albert S. Khouri, Staten Island, NY (US)

(72) Inventors: Richard F. Honigsbaum, Passaic, NJ (US); Albert S. Khouri, Staten Island, NY (US)

(*) Notice: Subject to any disclaimer, the term of this patent is extended or adjusted under 35 U.S.C. 154(b) by 0 days.

(21) Appl. No.: 16/768,335

(22) PCT Filed: Dec. 7, 2018

(86) PCT No.: PCT/US2018/064424
§ 371 (c)(1),
(2) Date: May 29, 2020

(87) PCT Pub. No.: WO2019/113420
PCT Pub. Date: Jun. 13, 2019

(65) Prior Publication Data
US 2020/0397564 A1 Dec. 24, 2020

Related U.S. Application Data

(60) Provisional application No. 62/595,876, filed on Dec. 7, 2017.

(51) Int. Cl.
*A61F 9/007* (2006.01)
*A61F 2/16* (2006.01)
*A61F 9/008* (2006.01)

(52) U.S. Cl.
CPC .......... *A61F 2/1624* (2013.01); *A61F 2/1678* (2013.01); *A61F 9/008* (2013.01); *A61F 9/00736* (2013.01); *A61B 2217/007* (2013.01); *A61F 2002/1682* (2015.04); *A61F 2002/1683* (2013.01); *A61F 2220/0008* (2013.01)

(58) Field of Classification Search
CPC .................... A61F 2/1624; A61F 2/167; A61F 2002/1682; A61F 2002/1683; A61F 2220/0008; A61F 9/00736; A61F 9/008; A61B 2217/007
See application file for complete search history.

(56) References Cited

U.S. PATENT DOCUMENTS

| | | | |
|---|---|---|---|
| 6,849,091 | B1 | 2/2005 | Cumming |
| 2009/0018652 | A1 | 1/2009 | Hermans et al. |
| 2014/0058507 | A1 | 2/2014 | Reich |
| 2016/0000558 | A1 | 1/2016 | Honigsbaum |
| 2016/0361157 | A1 | 12/2016 | Honigsbaum |
| 2017/0135809 | A1 | 5/2017 | Haddock |
| 2018/0161151 | A1 | 6/2018 | Honigsbaum |

*Primary Examiner* — Jennifer Dieterle
*Assistant Examiner* — Tiffany P Shipmon
(74) *Attorney, Agent, or Firm* — Cozen O'Connor

(57) ABSTRACT

Eye surgery methods which isolate segments of the eye capsule to which the relevant zonules are attached via a specially contoured capsulorhexis, and shrink-wrap these segments to the haptics of an AIOL to disaccommodatively actuate the latter, accommodative actuation of the AIOL being effected by an accommodative bias built into the AIOL, a tensioning ring, or both.

6 Claims, 12 Drawing Sheets

SHRINK-WRAP ANCHORED AND SHRINK-WRAPPED ACTUATED ACCOMMODATIVE INTRAOCULAR LENSES AND METHODS FOR IMPLANTATION THEREOF

PRIORITY CLAIM

This is a U.S. national stage of application No. PCT/US2018/064424, filed on Dec. 7, 2018. Priority is claimed on U.S. Provisional Application No.: 62/595,876, filed Dec. 7, 2017, the contents of which are incorporated herein by reference.

BACKGROUND OF THE INVENTION

1. Field of the Invention

The present invention relates to methods for modifying the capsule of an eye to shrinkwrap anchor and shrinkwrap actuate accommodative intraocular lenses (AIOLs), to AIOLs configured for shrinkwrap anchoring and shrink-wrapped actuation, and to methods for implanting AIOLs so configured into capsules so modified.

Specifically, the present invention relates to capsulorhexii specially configured to effect shrinkwrapping of the outboard end portions of the haptics of AIOLs that are specially configured for shrinkwrap anchoring and shrinkwrapped actuation by the remnants of capsules that survive the previously mentioned specially configured capsulorhexii.

2. Description of the Related Art

Some seventy years have elapsed since Sir Harold Ridley implanted a single-focus intraocular lens into the capsule of a human eye to restore distance vision lost to a cataractous crystalline lens and the extraction of that lens, and despite the obvious demand for an implant that is also accommodative and the best efforts of inventors and manufacturers of AIOLs to date to provide same, no presently available accommoative intraocular lens (AIOL) approved by the United States Food and Drug Administration (USFDA) or otherwise provides a combination of the level of accommodation and the quality of vision provided by a properly fitted pair of progressive eyeglasses.

AIOLs can, according to the prior art, be implanted into an eye from which the crystalline lens has been extracted, typically via anterior capsulorhexis, and either implanted directly into, and actuated by, the capsulorhexis-crippled capsule, or extra-capsularly and attached to and actuated directly by the ciliary body muscle.

An example of the former is published United States Patent Application 20090018652 to Hermans et al which discloses a two lens accommodative intraocular lens system for implantation into the capsule of an eye from which the crystalline lens has been extracted via capsulorhexis. and, because the Hermans AIOL maintains separation between the anterior and posterior capsules and thus prevents shrink-wrapping, continues to function accommodatively in the younger eyes for which it is intended, as confirmed by the functionality of Synchrony Vu™ AIOLs there. Synchrony Vu™ AIOLs are not, however, approved for implantation by the USFDA for even the limited market mentioned.

Borja et al., published United States Patent Application 20150173892A1, is a further example of an actuator much like that disclosed by Hermans. Neither Boria nor Hermance, however, disclose the specially contoured capsulorhexis nor anticipate the special haptics of the AIOLs of the present invention.

Prior art examples of ciliary muscle attached AIOLs include Ichikawa et al, published United States Patent Applications 20150305856A1, 20150305857A1 and 20150305858A1 the first two of which are single lens configurations in which the lens is shown as being translated anteriorly by contraction of the ciliary body muscle, and the third is a two-lens configuration in which the anterior lens is intended to function as the single lens of the first two and the posterior lens is anchored into the capsulorhexis-compromised capsule. Once again there is no hint or suggestion of the specially contoured capsulorexii or the bifurcated haptics of the AIOLs of the present invention.

Further, direct attachment of an AIOL to, and actuation by, the ciliary body muscle of an eye is not well tolerated, as confirmed by as confirmed by the literature re UGH Syndrome, e.g., E. L. Crowell, *Uveitis-Glaucoma-Hyphema Syndrome*, Eye Wiki (talk transcript) 2015 Nov. 30.

The present invention also includes configurations having anterior capsule tensioning rings, bifurcated haptic ATOLs and bellows-type hydraulic lenses, and these are mentioned (as are their initial disclosures) in published United States Patent Applications US20160000558A1, US20180161151A1, US20160361157A to Honigsbaum (one of the present inventors).

The present invention further includes bending grooves and pivots, and the former are described in Cumming, published U.S. Pat. No. 6,849,091 B1 and reduced to commercial practice in the Crystalens™ AIOL, and the latter in the Hermans application and the Synchrony VuSynchrony Vu™ AIOL respectively.

SUMMARY OF THE INVENTION

While ideally, AIOL actuation with respect to accommodation and disaccommodation would be effected by zonules detached from the capsule and attached to the haptics of an AIOL, the delicate nature of the zonules makes this an impossible task, and the present invention instead isolates segments of the capsule to which the relevant zonules are attached via a specially contoured capsulorhexis, and shrink-wraps these segments to the haptics of an AIOL to disaccommodatively actuate the latter, accommodative actuation of the AIOL being effected by an accommodative bias built into the AIOL, a tensioning ring, or both.

While the capsulorexii of the present invention retain enough of the anterior capsule to shrinkwrap the outboard ends of the haptics and thus actuate the AIOLs of this invention, they also remove enough of the anterior capsule between the haptic ends to prevent the kind of shrinkwrapping of anterior and posterior capsule remnants that, with traditional capsulorhexii, render prior art haptic actuated AIOLs virtually inoperative in a matter of months after implantation, as confirmed by *Aberrometry in patients implanted with Accommodaative Intraocular Lenses* Perez-Merino et al, Am J Ophthalmol: 2014 Feb. 13.

Because the capsulorexii appropriate for this invention are atypical with respect to cataractous crystalline lens extraction and IOL implantation, they are preferably cut with femtosecond lasers intended for ophthalmological purposes such as cutting conventional capsulorhexii, cataractous lens extraction, corneal reshaping, etc., but programmed to cut capsulorhexii in accordance with the present invention for the purpose, rather than asking the AIOL implant surgeon to do so manually.

The outboard ends of the haptics of this invention are also optionally ribbed, slotted or otherwise configured to effect retention not only by the previously mentioned shrinkwrapping, which takes a matter of weeks to complete, but also initially by gluing and/or mechanical means.

Thus, once anchoring is effective for its intended purpose, the centrifugal forces transmitted from the relaxed ciliary body muscle to the shrinkwrapped portions of the capsule by the zonules will maintain the AIOL in its disaccommodative state, and when the ciliary body muscle contracts as response to the need for accommodation, lower centrifugal forces transmitted to the capsule by the zonules will allow the centripetal forces provided by the remnants of the capsule, the accommodative bias of the AIOL, and an anterior capsule tensioning ring (if one is attached thereto) will effect accommodation of the AIOL.

BRIEF DESCRIPTION OF THE DRAWINGS

The following description, given with respect to the attached drawings, may be better understood with respect to the non-limiting examples of the drawings, wherein:

FIG. 9 are anterior plan views of anterior capsules upon which are superimposed laser-defined capsulorhexii cutting patterns and AIOLs appropriate with respect thereto, both in accordance with the present invention;

DETAILED DESCRIPTION OF THE EXEMPLARY EMBODIMENTS

The description and the drawings herein to which the description refers are for purposes of explanation and illustration and are not for limiting the scope of the invention. The scope of the invention is defined by the claims.

Figure 1:
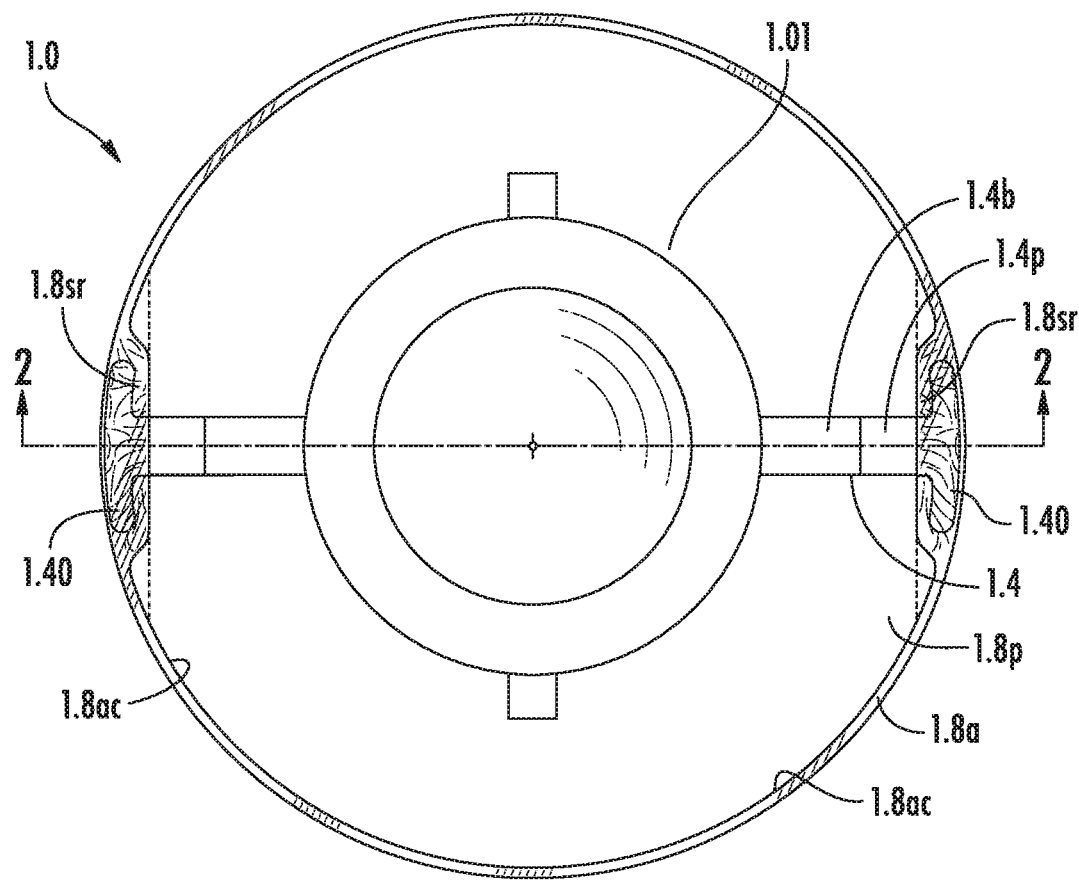
FIG. 1 is an anterior plan view of a lens capsule of an eye which has been modified via a specially contoured capsulorhexis, from which the crystalline lens has been extracted, and into which a bifurcated haptic AIOL has been implanted, all in accordance with the present invention.

FIG. 1 is an anterior plan view of the lens capsule of an eye in accordance with the present invention, is generally designated and identified by leader line 1.0, and from which a cataractous or otherwise defective crystalline lens has been extracted via a specially contoured anterior capsulorhexis 1.8ac, and into which accommodative intraocular lens 1.01 has been implanted. The outboard ends of its haptics 1.4 and their outriggers 1.40 are anchored to the remnants of capsule 1.8 by the shrink-wrapping 1.8sr of the surviving portions of anterior capsule 1.8a to posterior capsule 1.8p (the latter, of course, also specially contoured if appropriate).

Capsulorhexis 1.1ac follows the line so designated in the drawing and is shown curved around the shrink-wrapped portions 1.8sr of anterior capsule 1.8a. These curved-around portions may not, however, lie as flat as suggested by the drawing because of the elastic anterior capsule fibers that survive capsulorhexis, and it may instead be expedient to cut a capsulorhexis that follows the dotted lines shown in the drawing in regions intended for shrink-wrapping.

Figure 9A:
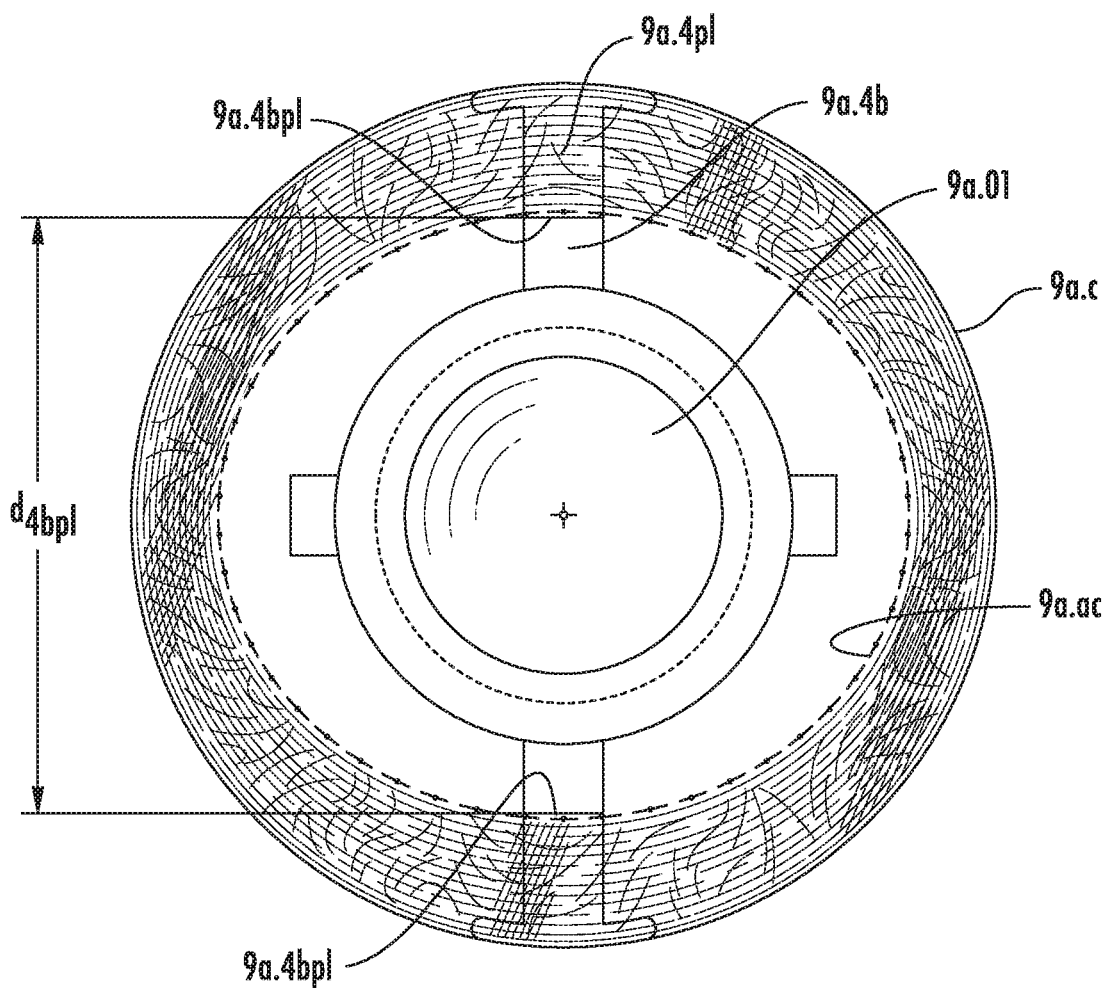
FIG. 9A is an anterior plan view of a capsule having an eliptical capsulorhexis, and into which is implanted an AIOL of FIG. 1, both in accordance with the present invention.

(Alternatives to the capsulorhexis shown in FIG. 1 are elliptical capsulorhexii such as shown in FIG. 9A, having a minor diameter that allows for the shrink-wrapping of the AIOL haptic ends and a major diameter that leaves no more than a millimeter (mm) or so of the anterior capsule. With any such configuration, however, the minor diameter of the capsulorexii must be large enough to confine the shrink-wrapping to the haptic outboard (plate) portions 9a.4p and avoid the shrink-wrapping the bifurcated haptic portions 9a.4b (1.4p and 1.4b of FIG. 1), which would, of course, render the AIOLs inoperative with respect to change from disaccommodation to accommodation or vice versa.)

AIOL 1.01 is actuated with respect to accommodation and disaccommodation by the contraction and relaxation of the surviving portions of the capsule, which is in turn actuated by the forces of contraction and relaxation of the ciliary body muscle as transferred to the capsule by the zonules, by the biasing of the AIOL (explained in the detailed descriptions of FIGS. 2 and 3), and by the centripetal forces provided by an optional tensioning ring affixed to the equator-proximal part of the anterior capsule that survives the specially contoured capsulorhexis cut in accordance with the present invention.

Figure 1A:
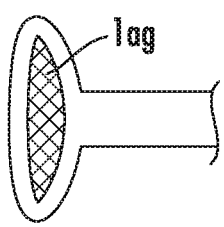
FIG. 1A is a plan view of "D" shaped alternative outboard ends for the haptics of FIG. 1.
Figure 1B:
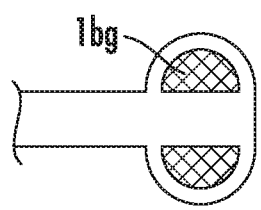
FIG. 1B is a plan view of loop-shaped alternative outboard ends for the haptics of FIG. 1.
Figure 10:
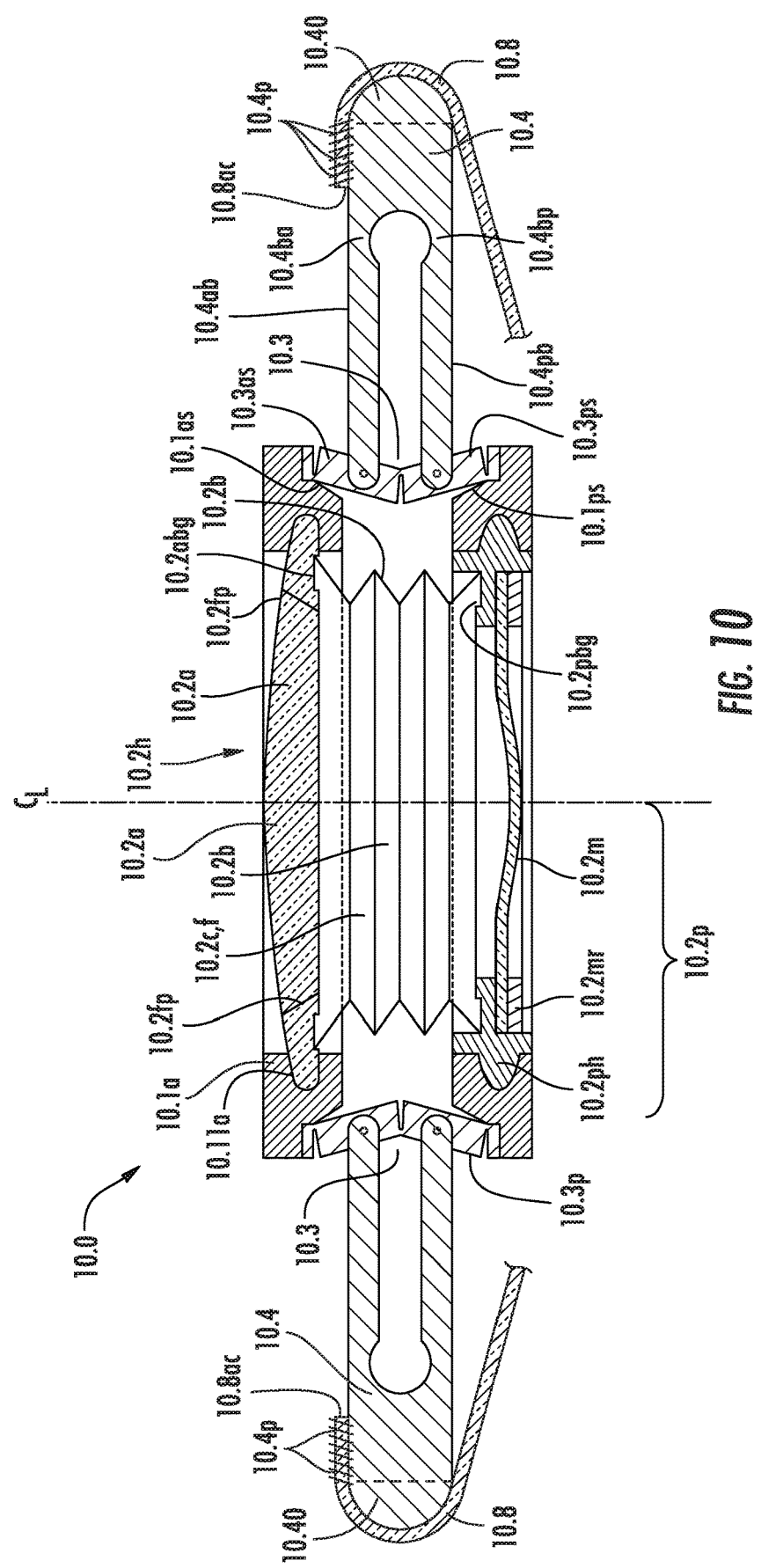
FIG. 10 is a sectional view of a hydraulic AIOL implanted in a capsule and anchored thereto and actuated thereby, all in accordance with the present invention.

FIGS. 1A, 1B and 10 are alternate outboard end configurations for haptics 1.4 of FIG. 1; FIG. 1A being a "D" shaped end, 1B a double "D", and 1C a "B", and the FIG. 1C configuration is presently preferred because each haptic end contacts the capsule circumferential region in two places, and thus better resists misalignment of the AIOL optical axis with respect to that of the eye.

Each of the haptic end configurations of FIGS. 1A, B & C also include optional open mesh grid-like portions 1ag, 1bg, 1cg to further facilitate shrink wrap anchoring of the haptic ends to the portions of the capsule that survive capsulorhexis, and these grid-like portions can be further coated with tissue-compatible surgical glue, fibrogen-like substances, etc., to hold the AIOL in place after implantation and during shrink-wrapping.

Figure 2:
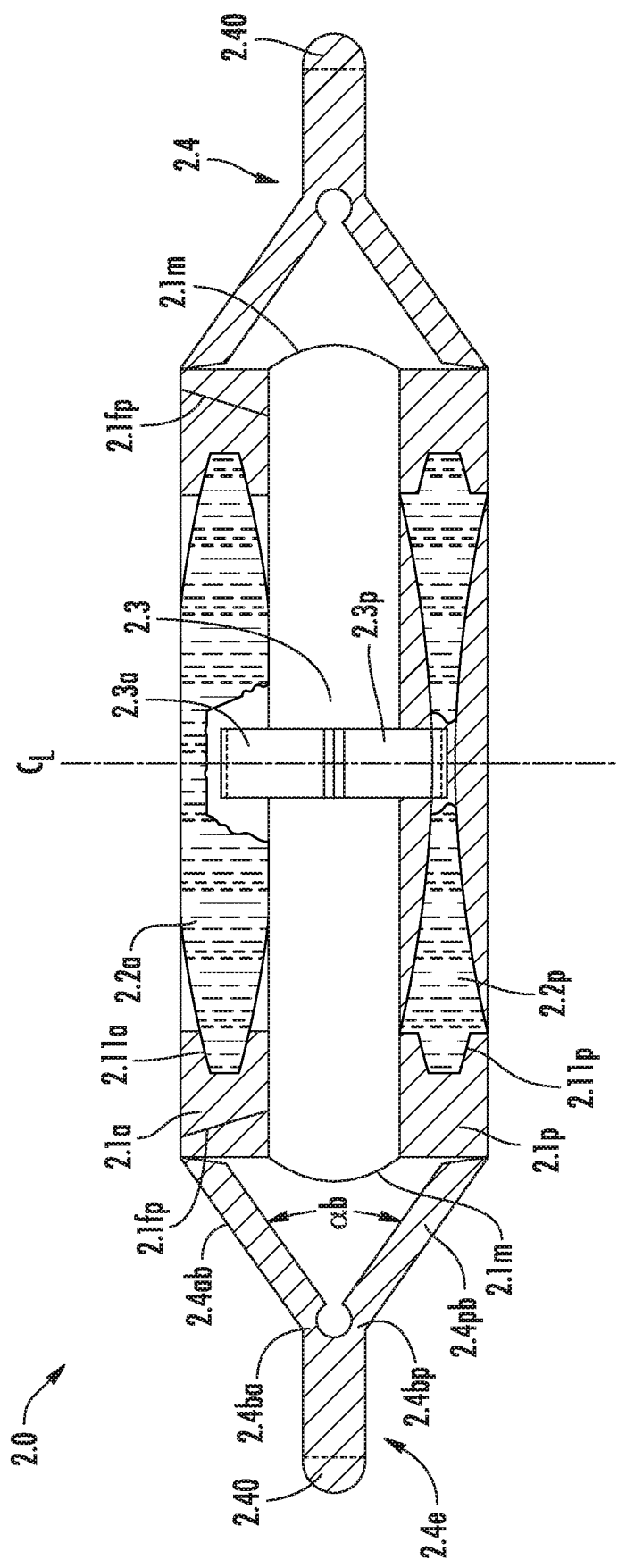
FIG. 2 is a sectional view of the AIOL of FIG. 1 defined by cutting plane line 2-2 of FIG. 1.

FIG. 2 is a sectional view of the AIOL of FIG. 1 as defined by cutting plane line aa of FIG. 1, and comprises anterior and posterior lens rings, 2.1a and 2.1p, lens grooves 2.11a and 2.11p into which are inserted biconvex lens 2.2a and biconcave lens 2.2p respectively, center-pivoted struts 2.3 the anterior and posterior portions 2.3a and 2.3p of which are pivotably connected to lens rings 2.1a and 2.1p respectively, and bifurcated haptics 2.4.

Center-pivoted struts 2.3 prevent tilt misalignment of the optical axis of lens 2.2a with respect to lens 2.2p, and vice versa.

Bifurcated haptics further comprise anterior branches 2.4ab, posterior branches 2.4pb, anterior biasing portions 2.4ba, posterior biasing portions 2.4bp and outriggers 2.4o, or their loop shaped equivalents shown in FIGS. 1A, 1B and 10 respectively. Biasing portions 2.4ba and 2.4bp preferably bias AIOL 2.0 accommodatively as an alternative to the centripetal capsular forces lost by capsulorhexis.

Also shown in FIG. 2 is optional elastic membrane 2.1m which is intended to isolate the portion of the space between anterior and posterior lenses 2.2a and 2.2p from the aqueous humor, and thus prevent the survival and reproduction of epithelial cells left over from crystalline lens extraction by depriving them of nutrients and a scaffold for growth otherwise provided by the aqueous humor and capsule remnants respectively. Thus the space defined by membrane 2.1m, lens rings 2.1a,p and lenses 2.2a,p is preferably occupied by a sterile cell-free saline solution having an index of refraction substantially equal to that of the aqueous humor, and that space is accessible for purposes of filling and purging of bubbles, etc., via fill-purge ports 2.1fp.

Figure 3:
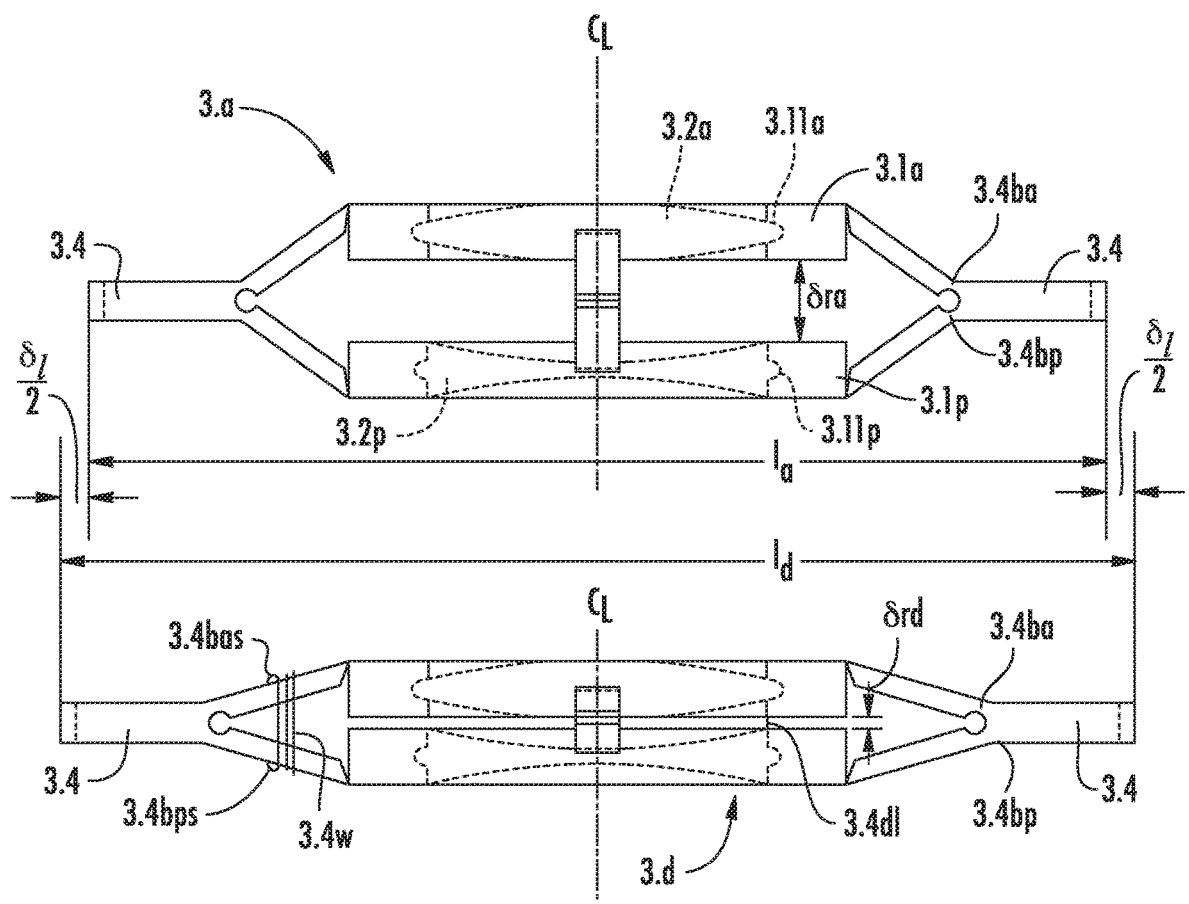
FIG. 3 are elevational views of the AIOL of FIG. 1 in a direction normal (perpendicular) to cutting plane aa of FIG. 1.
Figure 3A:
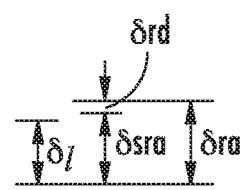
FIG. 3a is an illustration of the change in lens spacing resulting from an arbitrary change in the spacing between the haptic outboard ends of FIG. 1.

FIGS. 3 and 3A comprise an accommodated version of FIG. 2 here identified by leader line 3.a and a disaccommodated version here identified by leader line 3.d, and the primary purpose of the drawing is to make clear the change in the spacing between biconvex anterior lens 3.2a and biconcave lens 3.2p and thus the change in accommodation effected by the change in spacing between the outboard ends of haptics 3.4, and this is summarized in FIG. 3a, from which it is clear that the change in lens spacing (which is the same as the change in ring spacing $\delta$sra ($\delta$sra=$\delta$ra−$\delta$rd) is about 13% greater than the change in the spacing between the outboard ends of haptics 3.4 $\delta$l.

The bifurcated haptics of lens assemblies 3a, 3b, however, include biasing portions 3.4ba and 3.4bp and the biasing effect of membrane 2.1m, and the first two biasing portions mentioned at least are preferably configured to bias the AIOL accommodatively and thus replace at least a part of the accommodative centripetal forces provided by the capsule in an emmetropic eye, but lost by capsulorhexis, and thus, perhaps, obviate the need for a tensioning ring.

AIOL implantation in accordance with the present invention, however, also requires the haptic ends to fully engage the capsule equator and to remain so engaged for the time needed to properly effect the shrink-wrapping shown as 1.8sr in FIG. 1.

While the eye can be so-maintained by the use of a disaccommodation mimetic such as homatropine hydrobromide, the accommodative biasing of the AIOL must also be addressed, and is so-addressed by wrapping of absorbable suture material 3.4w held in place by spurs 3.4bas, 3.4bps or, as presently preferred, by a non-absorbable suture or other material 3.4dl that is accessible for severing by a laser beam when the shrink-wrapping 1.8sr of FIG. 1 is complete. While laser severing requires an additional level of skill, it is presently preferred because the debris field resulting from the absorbable suture material can cause inflammation and/or clog the drainage path for aqH.

(Disaccommodative implantation and the subsequent restoration of accommodative capability is, of course, also appropriate for embodiments of FIGS. 2, 4, 5, 6, etc., and is effected analogously.)

Figure 4:
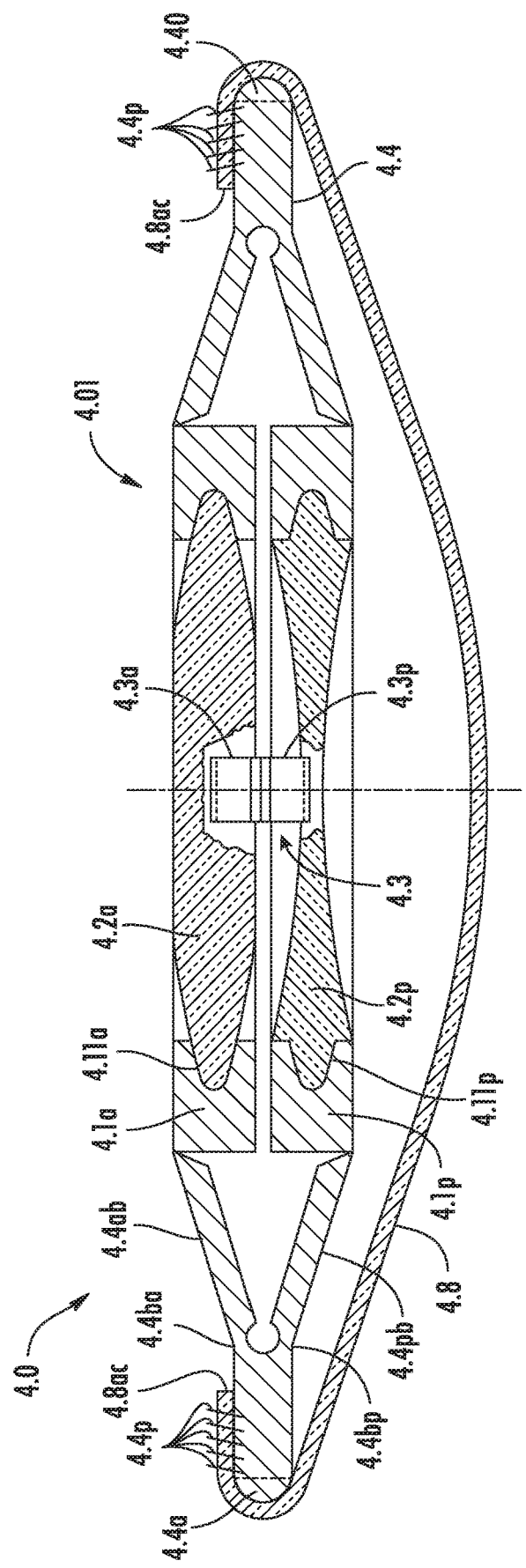
FIG. 4 is a sectional view of both the AIOL and the capsule of FIG. 1 as defined by cutting plane line 2-2 of FIG. 1.

FIG. 4, generally designated by leader line 4.0, shows an AIOL 4.01, much like AIOL 2.0 of FIG. 2, except that AIOL 4.01 is shown as disaccommodative and implanted in and anchored to capsule 4.8, which also has had an anterior capsulorhexis 4.8ac to allow for the implantation of AIOL 4.01 (and, of course, extraction of a cataractous or otherwise compromised crystalline lens) while AIOL 2.0 of FIG. 2 is merely shown as free-standing and accommodative.

(AIOL 4.01, it should be noted, is not shown in contact with capsule 4.8, equatorial regions excepted, because the posterior zonules (not shown) insert at the anterior hyaloid membrane before inserting at the anterior capsule, and thus maintain the spacing shown.)

Familiar from FIG. 2 are anterior and posterior lens rings 4.1a, 4.1p, anterior and posterior lens grooves 4.11a, 4.11p retaining anterior and posterior lenses 4.2a, 4.2p respectively, bifurcated haptics 4.4 comprising anterior and posterior branches 4.4ab, 4.4pb, biasing portions 4.4ba, 4.4bp, center pivoted struts 4.3 having anterior and posterior segments 4.3a, 4.3p, etc.

Figure 7A:
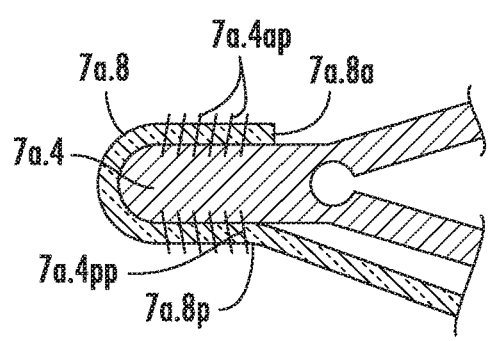
FIGS. 7A through 7G are detailed sectional views of the haptic end portions of the AIOLs of this invention as modified to effect gluing and/or mechanical attachment to the surviving portions of a capsule, all in accordance with this invention.

AIOL 4.01 is, however, shown attached to portions of anterior capsule 4.8a that survive capsulorhexis 4.8ac (which, as shown in the drawing, is of large enough diameter to avoid the shrink-wrapping of the bifurcated portions of the haptics) by a plurality of anterior capsule penetrators 4.4p, the posterior end of each of which is partially embedded in an outboard end portion of haptics 4.4 and the anterior end of each of which penetrates a surviving portion of anterior capsule 4.8a to mechanically couple the former to the latter as shown. (Penetrators can additionally, of course, be embedded into the posterior haptic faces, and if so, would penetrate adjacent portions of the posterior capsule, as shown in FIG. 7A, but would not be long enough to damage the hyaloid membrane.)

Penetrators 4.4p are preferably not perpendicular to the haptic portions in which they are embedded, and are not shown as such in the drawing. They are instead preferably canted (tilted) centripetally to better resist being dislodged from their intended positions with respect to capsule 4.8 during shrink-wrap anchoring.

AIOLs with penetrators do, however, require special techniques and special haptic outboard ends to properly insert the penetrators into the appropriate parts of the capsules that survive the specially contoured capsulorhexii, and these are illustrated and described with reference to FIGS. 5, 6 and 7, as are penetrator tilt angles appropriate thereto.

Figure 5:
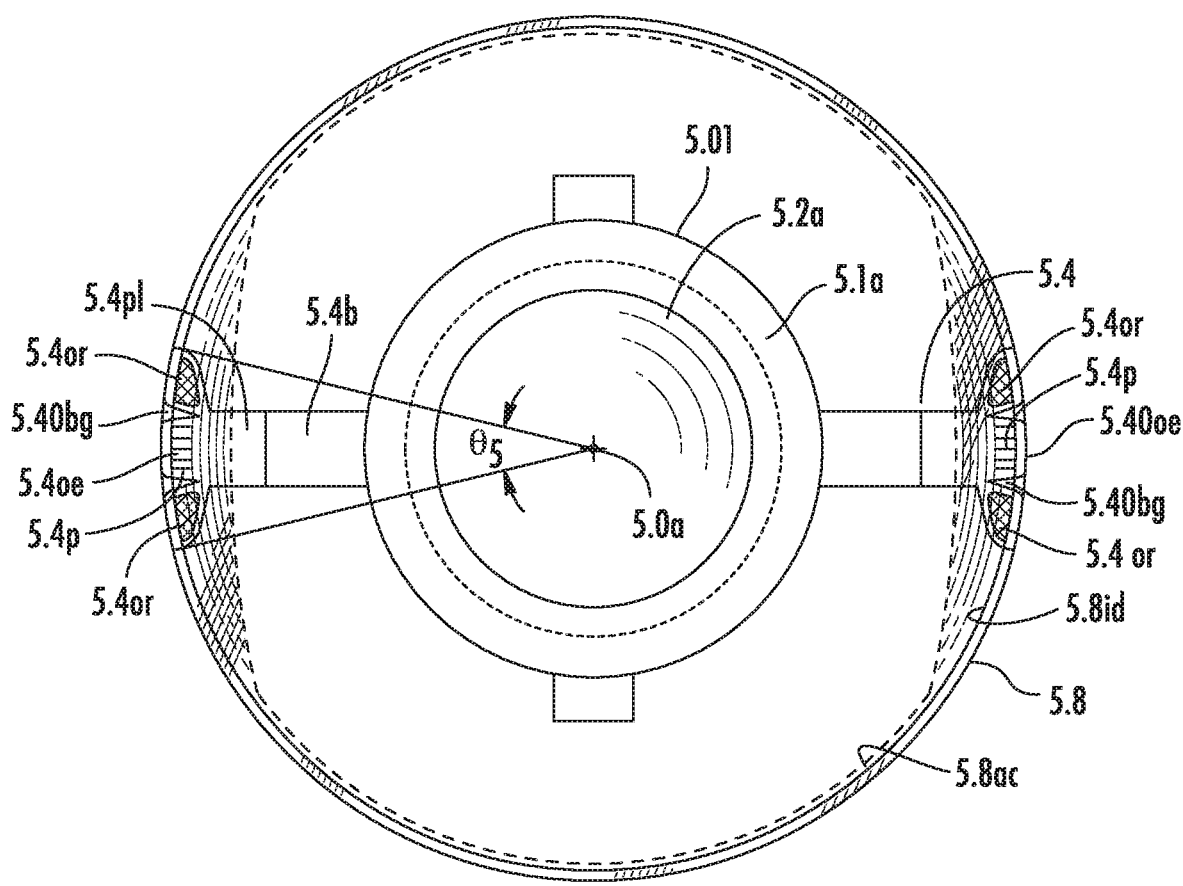
FIG. 5 is an anterior plan view of a bifurcated haptic AIOL implanted in a capsule, the haptic outboard ends if the AIOL of which have been modified to effect both mechanical and shrinkwrap anchoring of the AIOL to the surviving remnants of the capsule, all in accordance with the present invention.

FIG. 5 shows an AIOL 5.01 in accordance with the present invention and implanted in a capsule 5.8 having a specially contoured anterior capsulorhexis much like that shown dotted in FIG. 1, but before shrink-wrapping, and here again the capsulorhexis is specially contoured to prevent shrink-wrapping of the bifurcated portions 5.4$b$ of haptics 5.4.

AIOL 5.01, however, unlike AIOL 1.01 of FIG. 1, has outriggers 5.4$or$ that are attached to the haptic outboard end portions (plate portions 5.4$pl$) by bending grooves 5.40$bg$ that are biased to extend outriggers 5.$or$ radially outward with respect to the lens portions of the AIOL.

Thus, when AIOL 5.01 is implanted in a capsule prepared as mentioned, and its haptics are urged farther in a disaccommodative direction by pressure applied to anterior lens 5.2$a$, anterior lens ring 5.1$a$, etc., by the surgeon, outriggers 5.4 will bend to the configuration shown in FIG. 5, and when the aforementioned pressure is relaxed, penetrators 5.4$p$ will engage and grip the remnants of anterior capsule 5.8$a$ as shown in FIG. 4 (as will posterior penetrators as shown in FIG. 7A, if present.)

Figure 1C:
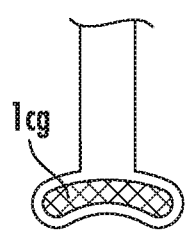
FIG. 1C is a plan view of "B" shaped alternative ends for the haptics of FIG. 1.
Figure 5A:
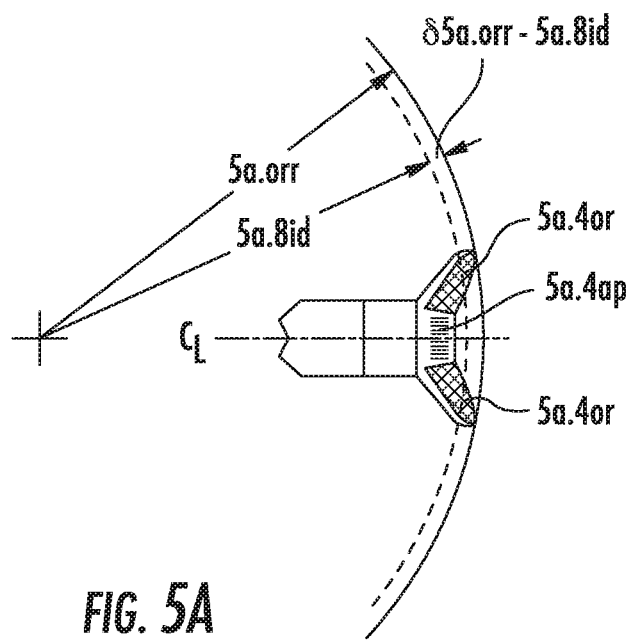
FIG. 5A is a detail plan view of a haptic of the AIOL of FIG. 5 before implantation.

Outriggers 5.4 also optionally include gridded portions 5$a.g$ in FIG. 5A which, like the gridded portions of FIGS. 1A, 1B, 1C serve to further facilitate shrink-wrap anchoring.

Figure 6:
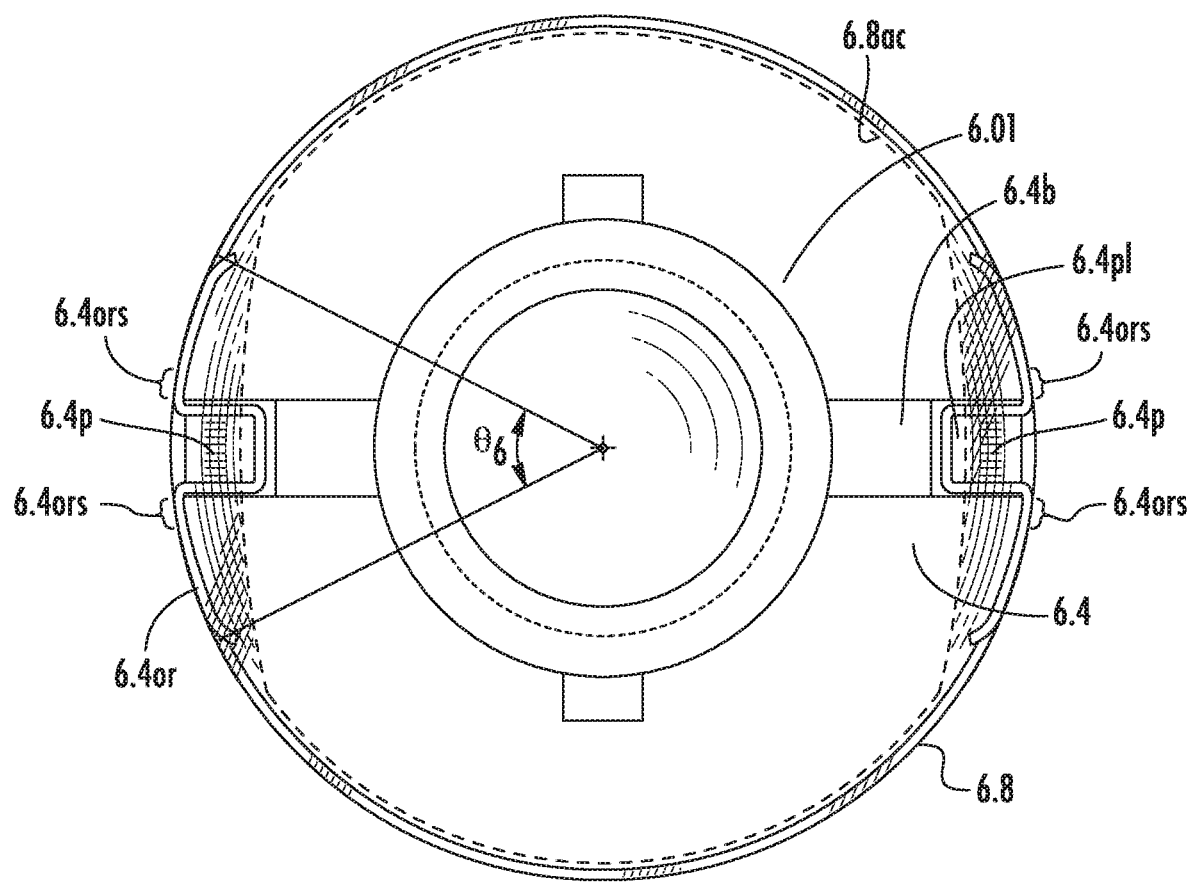
FIG. 6 is an anterior plan view of a bifurcated haptic AIOL implanted in a capsule, the haptic outboard ends of the AIOL of which include outriggers for shrinkwrap anchoring and actuation of the AIOL, all in accordance with the present invention.
Figure 6A:
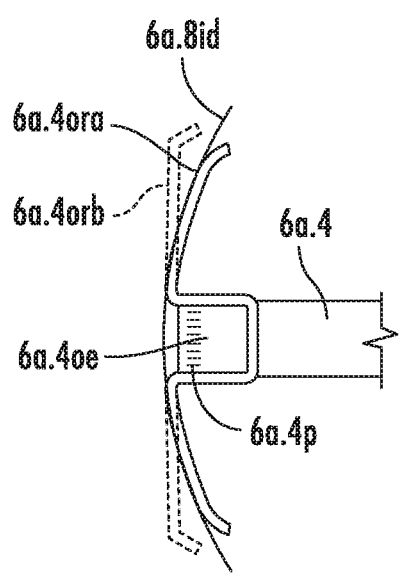
FIG. 6A is a detail plan view of an outboard end of a haptic of the AIOL of FIG. 6 both before and after implantation.

FIG. 6 is an arrangement much like that of FIG. 5 (with the same proscriptions with respect to shrink-wrapping the bifurcated portions of the haptics) excepting, of course, the haptic end portion outriggers, which here are longer, and are flexible enough to be contoured upon implantation by the inner portion of capsule equator 6.8, as shown in greater detail in FIG. 6A, but stiff enough to transmit forces applied to capsulorhexis-modified capsule 6.8 by zonules (not shown) to haptics 6.4 of AIOL 6.01.

Comparing angle θ5 of FIG. 5 with θ6 of FIG. 6, it is clear that θ6 is larger, as is the fraction of the total centrifugal zonular force available to disaccommodate AIOL 6.01 via forces transmitted to haptics 6.4 by the remnants of capsule 6.8 that survive specially contoured anterior capsulorhexis 6.8$ac$, and also posterior capsulorhexis 6.8$pc$ if cut. (There is, however, a useful upper limit to angle θ6 because zonular centrifugal forces substantially perpendicular to haptics have little if any effect with respect to accommodation.)

Effective use of this additional centrifugal zonular force, however, requires haptic outriggers 6.4 or that allow for the change in capsular equatorial diameter from accommodation to disaccommodation and vice versa, and this is addressed by at least one of a slippery outrigger coating (e.g. Teflon™), elastic outrigger sleeves, and outriggers 6.4$or$ comprising tension springs.

AIOL 6.01 of FIG. 6 is anchored to appropriate portions of capsule 6.8 that survive capsulorhexis in much the same way that AIOL 5.01 is anchored to surviving portions of capsule 5.8, except that here the forces needed implant penetrators 6.4$p$ into the portions of capsule 6.8 that survive capsulorhexis are provided by an intentionally stiffened short section 6.4$ors$ of outriggers 6.4$or$.

FIG. 7 are fragmentary sectional views of the haptic outboard ends of FIGS. 4, 5, 6 etc., and show some of the special features of this invention such as the penetrators, the glue retention grooves, etc., in greater detail.

FIG. 7A makes it clear that the outboard ends of FIGS. 4, 5, 6 etc. can have not only anterior face penetrators 7.4$aap$ that penetrate anterior capsule portions that survive a specially contoured capsulorhexis, but also posterior face penetrators 7.4$app$ that penetrate surviving posterior capsule portions as well. (Posterior penetrators 7.4$app$, however, have shorter penetration portions than do anterior penetrators 7.4$aap$, this, as previously mentioned herein, to prevent damage to the anterior hyaloid membrane).

Figure 7B:
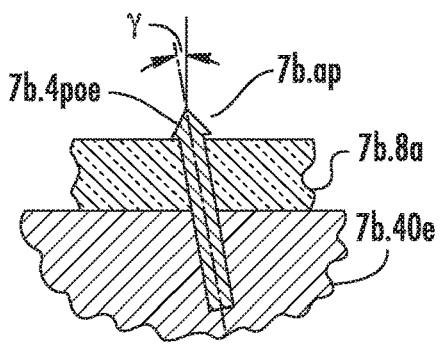

FIG. 7B is a detailed sectional view of an anterior penetrator of FIG. 7$a$, here identified by leader line 7$b.ap$, partially embedded in haptic outboard end portion 7$b.4oe$, and having penetrated anterior capsule fragment 7$b.8a$. Penetrator 7$b.ap$ as shown here also includes an optional outboard end 7$b.4poe$ which is in effect a barb of rotation, and which anchors anterior capsule fragment 7$b.8a$ of FIG. 7$a$ to haptic outboard portion 7$b.4oe$, or, if in the posterior face of haptic 7$a.4$, to posterior capsule 7$a.8p$. Penetrator outboard ends such as 7$b.poe$ can, however, weaken capsules, especially if on adjacent penetrators, and their use on every penetrator is, for this reason, discouraged.

Figure 7C:
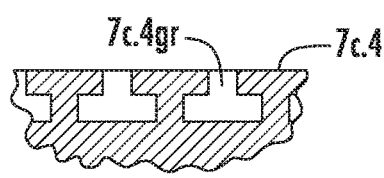
Figure 7D:
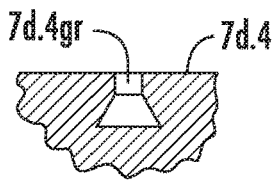
Figure 7E:
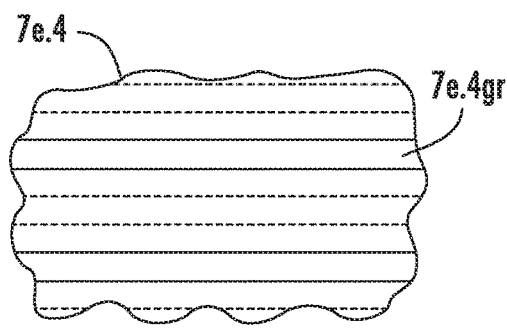
Figure 7F:
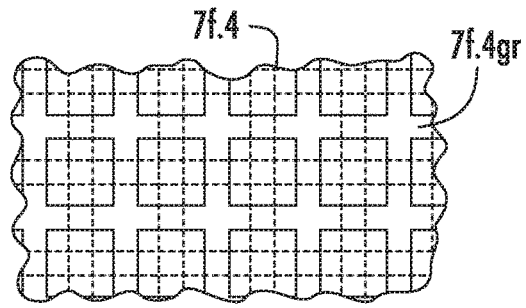
Figure 7G:
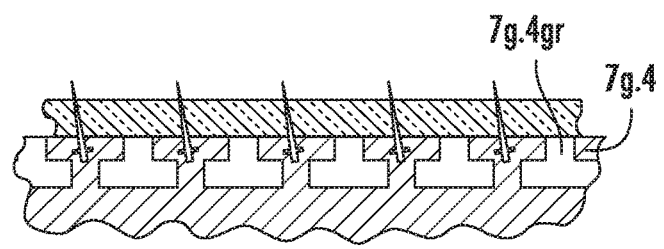

FIG. 7B also shows an angle gamma between penetrator 7$b.4p$ and a line normal to haptic 7$b.4$ of 10 degrees, as do FIGS. 4, 7A and 7G, and angles common to all of the penetrators of an AIOL of this invention of up to about 15 degrees would also be acceptable, this despite the fact that in applications other than the present one such angles are typically significantly greater. The smaller angle is, however, appropriate here because capsular elasticity will seat the penetrators, and significantly larger angles would require excessive force to be applied to an anterior ring or lens to seat the penetrators via methods described with reference to FIGS. 5 and 6 herein.

FIGS. 7C, D and G are fragmentary sectional views of haptic outboard ends showing glue retention grooves 7$c.4gr$, 7$d.4gr$, 7$g.4gr$, FIGS. 7E and F, are plan views thereof, and FIG. 7$g$ embodiments, which include provision for initial anchoring of the AIOLs of this invention by both gluing and the insertion of penetrators into portions of the capsules that survive capsulorexii, are, for this reason, presently preferred.

The present glue application, however, differs from conventional surgical glue applications in that the intended bond is one between human tissue (the aforementioned capsule fragments) and the man-made haptic outboard ends, and grooves 7C, D, eE, F and G, and texturing of the corresponding haptic surfaces, facilitate bonding to the haptics.

Glues approved for surgical use include those that are fibrinogen based, those that are silicone based, and those that are acrylic; and of these only the acrylic glues are routinely used ophtalmologically, e.g., to repair corneal tears. While fibrinogen based glues would seem to be the obvious choice because they would encourage the shrink-wrap anchoring of the present invention, they risk fibrosing of the aqH drainage path, and any such use is presently discouraged unless and until their safe use has been validated experimentally.

While the biocompatibility of glue, its suitability for the purpose mentioned without adversely affecting the eye or any parts thereof has been specifically mentioned herein, the biocompatibility of the AIOLs and their components, including the penetrators, is a requirement of this invention as well, and is addressed in published United States Patent Applications US20160000558A and US20160361157A mentioned earlier herein, the first of which is for tensioning rings, the penetrators of which are appropriate for use as such here.

Figure 8:
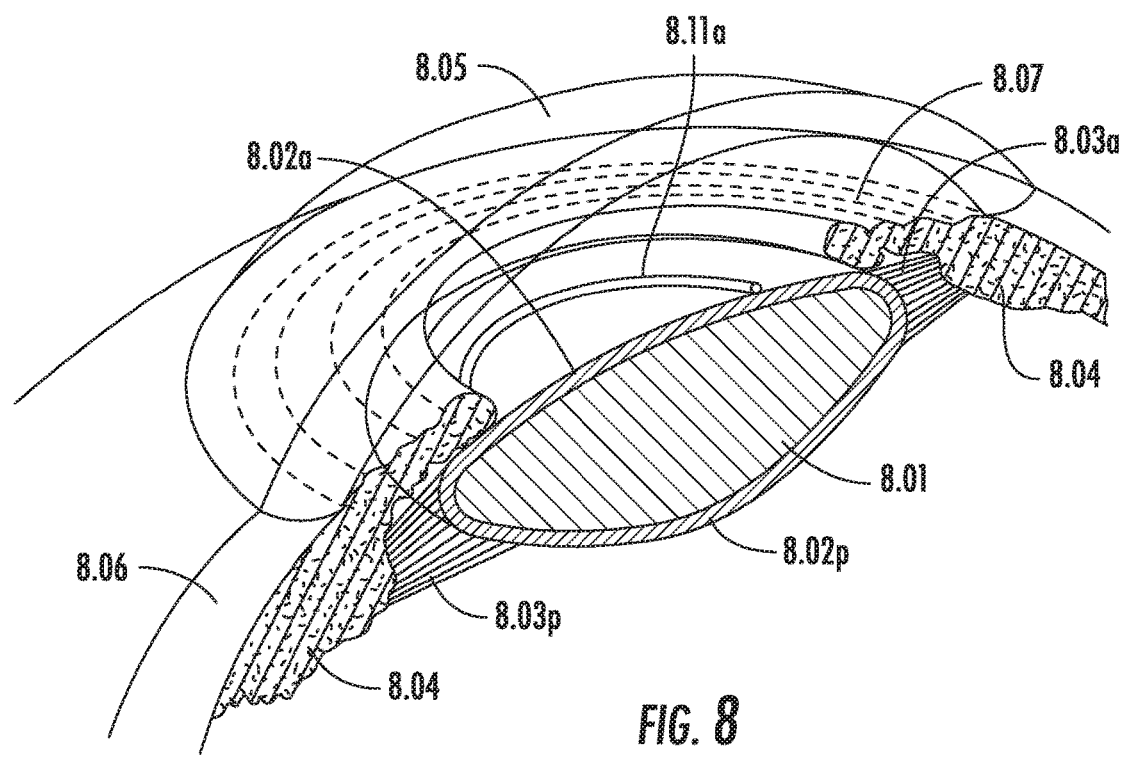
FIG. 8 is a prior art sectional pictorial drawing (derived from the prior art) of a capsule to which a tensioning ring has been attached before crystalline lens extraction.
Figure 8A:
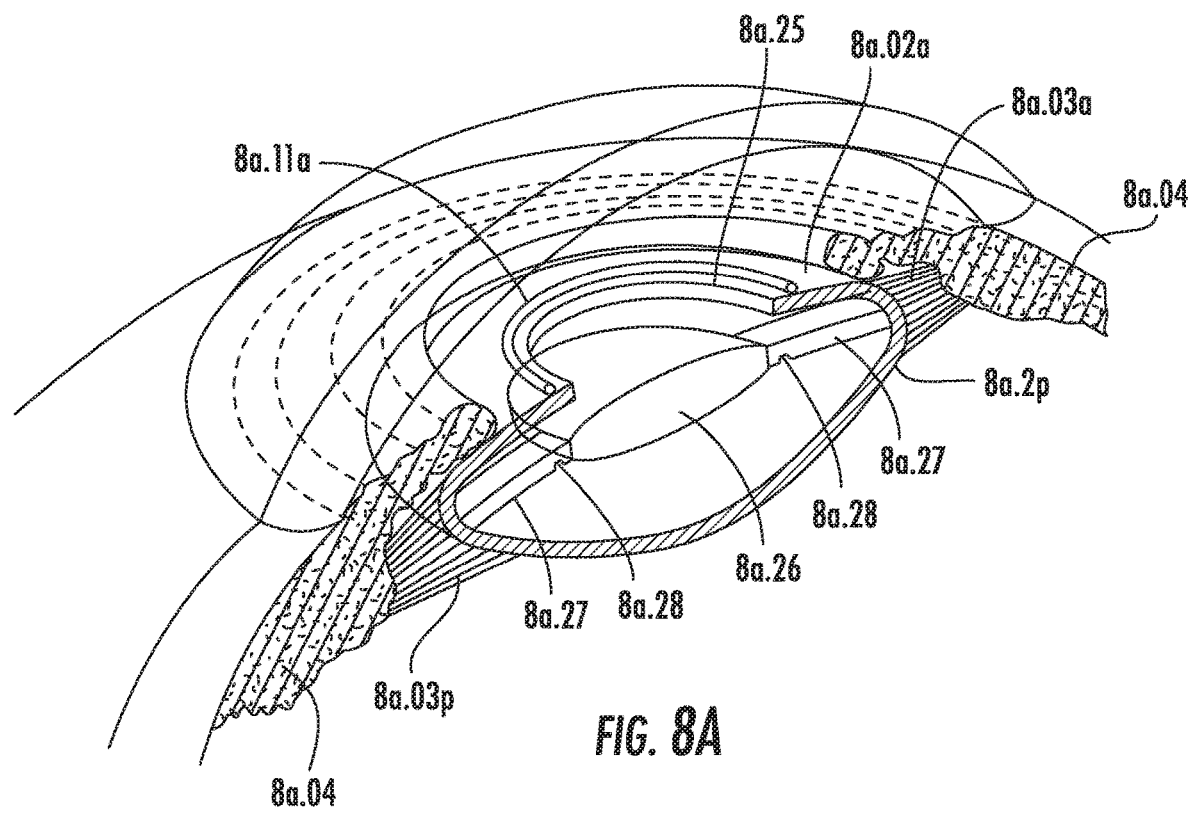
FIG. 8A is a prior art sectional pictorial drawing (derived from the prior art) of the capsule of FIG. 8 after extraction of the crystalline lens and the implantation of a prior art AIOL.

FIGS. 8 and 8A are pictorial drawings of an eye, each partially cut away to show features of interest with respect to the present invention. FIG. 8 shows a lens capsule before extraction of cataractous crystalline lens 8.01, and to anterior capsule 8.02a of which has been attached anterior capsule tensioning ring 8.11a. Other items of interest with respect to the present invention include anterior and posterior zonules, 8.03a and 8.03b respectively, ciliary body muscle 8.04, and posterior capsule 8.02b.

FIG. 8A shows the eye of FIG. 8 after extraction of cataractous crystalline lens 8.01 of FIG. 8 via capsulorhexis 8a.25, phacoemulsification, etc., and the implantation of AIOL 8a26, 27 and 28. FIGS. 8a and 8b also make clear that the positioning of the anterior capsule tensioning ring (8a.11a in FIG. 8a; 8b.11a in FIG. 8b) is proximal to capsulorhexis 8a.25.

Figure 9B:
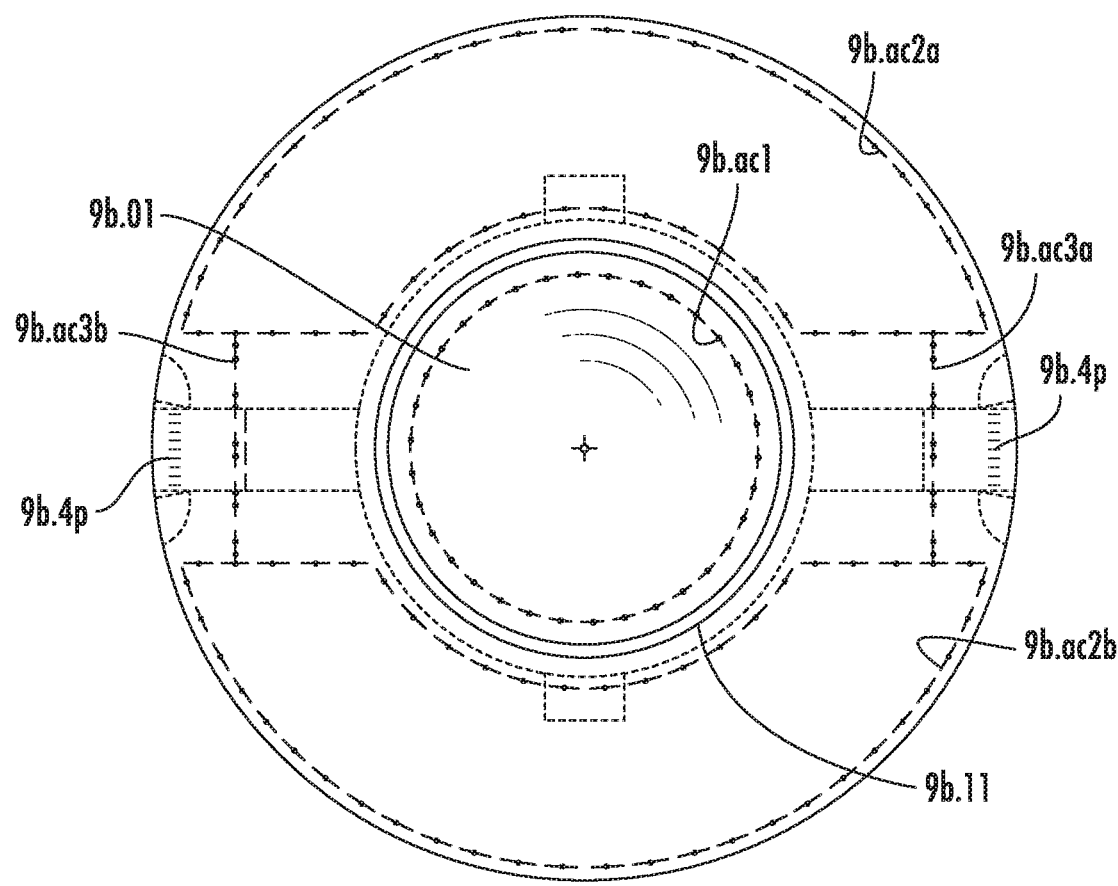
FIG. 9B is an anterior plan view of a capsule upon which are superimposed both an outline of a FIG. 5 AIOL and cutting patterns for capsulorhexii appropriate for the inplantation into the capsule of a FIG. 5 AIOL, both in accordance with the present invention.
Figure 9C:
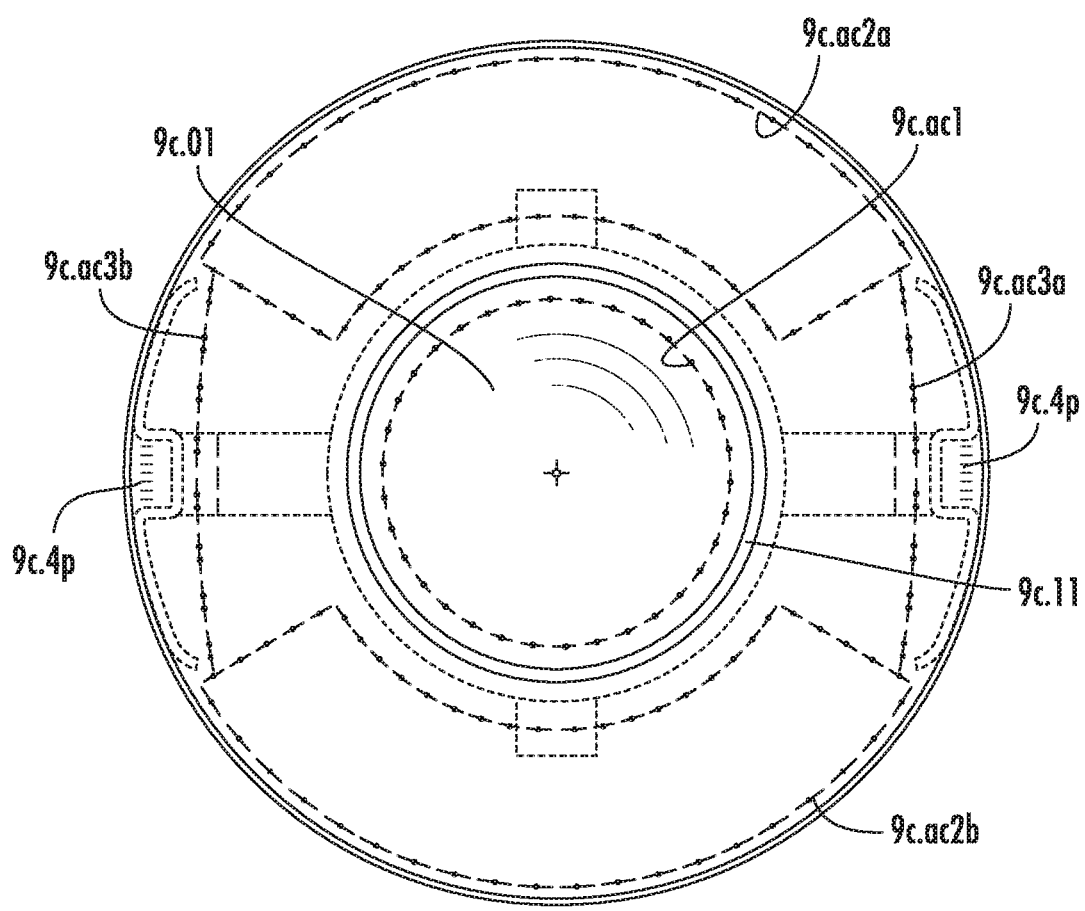
FIG. 9C is an anterior plan view of a capsule upon which are superimposed both an outline of a FIG. 6 AIOL and cutting patterns for capsulorhexii appropriate for the inplantation into the capsule of a FIG. 6 AIOL, both in accordance with the present invention.

FIGS. 9A, 9B and 9C are anterior plan views of capsules of eyes from which cataractous or otherwise compromised crystalline lenses have been fragmented and extracted and replaced with AIOLs of this invention (shown in outline by short dashed lines in FIGS. 9A, 9B and 9C) via anterior capsulorhexii and a small incision (not shown) at the edge of the cornea, as described in detail in method two herein.

Anterior capsulorhexii for the purposes of crystalline lens extraction and AIOL implantation are shown in FIGS. 9A, 9B and 9C as long-dash lines superimposed upon which are tiny circles to suggest that the capsulorhexii (rhexii) paths are defined by a plurality of cavitation pitts fsl laser "burned" into the anterior capsules to provide "tear on the dotted line" paths for tearing free the portions of the anterior capsules to be removed for purposes of this invention.

Anterior capsule capsulorhexii for the implantation of AIOLs 9a.01, (1.01 of FIG. 1) are preferably elliptical anterior capsulorhexii such as 9a.ac of FIG. 9a, the minor diameters of which are at least as great as the disaccommodated distance [d sub 4bpl] between the lines of demarcation 9a.4bpl between the bifurcated portions 9a.4b and the plate portions 9a.4pl of the haptics.

The preferred method for implantation of lens 9a.01 is method one, described in detail later herein, Once implantation is completed shrink-wrap will commence, the result being a configuration such as shown in FIG. 9a, While the AIOLs of FIGS. 4, 5 and 6 could also be implanted in capsules having capsulorhexii as per 9a.ac of FIG. 9A, initial anchoring via penetrators 4.4p, 5.4p and 6.4p of FIGS. 4, 5 and 6 respectively would be compromised by anterior capsules made floppy by such capsulorhexii, and the AIOLs of FIGS. 4. 5 and 6 are, for this reason, preferably implanted via method two, and into capsules having anterior capsulorhexii in accordance with FIG. 9B or 9C as appropriate.

FIG. 9B is an anterior plan view of a capsule of an eye from which a cataractous or otherwise defective crystalline lens (not shown in the drawing) is to be extracted, and into the space provided thereby is to be implanted an AIOL in accordance with FIG. 5 of this invention, designated by short dash lines in FIG. 9b, the AIOL to be implanted via method two of this invention, which includes the temporary implantation of tensioning ring 9b.11 to address the "floppyness" of the anterior capsule resulting from crystalline lens extraction and thus facilitate initial anchoring of AIOL 9b.01 of FIG. 9B as explained with reference to FIG. 5.

FIG. 9C is again an anterior plan view of a capsule of an eye from which a cataractous or otherwise defective crystalline lens (not shown in the drawing) is to be extracted as per FIG. 9b, but into which an AIOL in accordance with FIG. 6 rather than FIG. 5 of this invention, again designated by short dash lines, is to be implanted via method two of this invention, which includes the temporary implantation of tensioning ring 9c.11 to address the "floppyness" of the anterior capsule resulting from crystalline lens extraction, and thus facilitate initial anchoring of AIOL 9c.01 of FIG. 9C as explained with reference to FIG. 6.

FIG. 10 is a sectional view of a bifurcated haptic hydraulic accommodative intraocular lens (HAIOL), identified by leader line 10.0 in the drawing, and which, like the two-lens AIOL of FIG. 4 herein, is familiar from the prior art mentioned earlier herein excepting the haptics, which are modified in accordance with the present invention.

The HAIOL is shown contained within, and anchored to, capsule 10.8, the capsule having a capsulorhexis 10.8ac contoured in accordance with the present invention; and again, like the AIOL of FIG. 4, the HAIOL of FIG. 19 is shown anchored thereto by penetrators, here identified by leader lines 10.4p, and which are partially embedded into haptics 10.4. and penetrate capsule 10.8 as shown. (Initial anchoring can, of course, also or additionally be effected by gluing, as explained in detail earlier herein.)

FIG. 10 embodiments, like those of FIG. 4, are biased accommodatively by haptic 10.4 biasing portions 10.4ba, 10.4bp, but are implanted disaccommodatively, and are made so for the purpose by withdrawing refractive hydraulic fluid 10.2c,f via fill-purge ports 10.2fp, which is, of course, replaced as appropriate therethrough. Initial anchoring, the implantation of penetrators 10.4p into portions of anterior capsule 10.8ac that survive capsulorhesix, is effected by again withdrawing hydraulic fluid 10.2c,f and replacing same after anchoring via fill-purge ports 10.2fp.

The AIOLs if this invention are implanted into capsules of eyes to replace cataractous or otherwise compromised crystalline lenses extracted for the purpose, and preferably by one of two methods: implantation method one (Im1) comprising anchoring the AIOL to portions of capsules that survive capsulorhexis by shrink-wrapping alone, making the accommodative feature of the AIOL unavailable until shrink-wrap anchoring is substantially complete, and requiring the instillation of eye drops that not only dilate the ciliary body muscle but also the iris thus virtually guaranteeing patient non-compliance, and implantation method two (Im2), the surgery for which is somewhat more complicated, that additionally anchors the AIOL initially, making the accommodative feature of the AIOL available immediately following surgery.

Thus at least two distinct procedures, both of which are described in step-by-step detail herein, and both of which share the same broad steps of preparation for surgery, preparation for initial discharge, and aftercare, the first procedure comprising the substeps of:

Prep step 1: clearing the patient for the surgery.
Prep step 2: clothing the patient appropriately for the surgery.
Prep step 3: signing an informed consent document for the surgical procedure intended by both the patient and the surgeon.
Prep step 4: checking the patient's vital signs, and monitoring same if a general anesthesia is to be used.
Prep step 5: anesthetizing one of the patient or just the eye.
Prep step 6: inserting an eyelid separator (speculum).

The second procedure comprising the substeps of:
Initial discharge step 1: checking the patient's vital signs, or if continuously monitored and normal, removing the monitoring device(s).

Initial discharge step 2: removing the eyelid separator (if not previously removed).
Initial discharge step 3: scheduling follow-up appointments.
Initial discharge step 4; writing prescriptions, which for procedure 1 includes not only an antibiotic and an anti-inflammatory, but also a ciliary body muscle dilator.
Initial discharge step 5: instructing the patient and/or the caregiver re aftercare.
Initial discharge step 6: clothing the patient for travel.
Initial discharge step 7: confirming patient travel arrangements.

The third, aftercare comprising the steps of:
Aftercare step 1 examining the eye for adverse effects of the surgery preferably the day after surgery,
Aftercare step 2 monitoring shrink-wrap anchoring on a biweekly basis,
Aftercare step 3 unlocking the AIOL disaccommodative lock if still locked when shrink-wrap anchoring is substantially complete,
Aftercare step 4 final discharge.

AIOL Implantation Method One (Im1): AIOL Anchoring by Shrink-Wrapping Alone.
Step 1 patient preparation,
step 2 removeably affixing an fsl laser to a conjunctiva of the eye,
step 3 delineating via a plurality of fsl cavitation burns an elliptical guide to provide a "tear on the dotted line" feature on the anterior capsule capsulorhexis centered with respect to the optical axis \of the eye and having a major diameter of 1.5-2 mm (millimeters) less than an equatorial diameter of the capsule and a minor diameter at least that of a disaccommodated distance between the outboard ends of the bifurcated portions of the haptics of the AIOL, (FIG. 9A leader line 9a.ac),
step 4 (alternative to Im1 step 7) fsl cavitation cracking or otherwise preparing a cataractous or otherwise defective crystalline lens for extraction,
step 5 cutting at least a first small incision at an edge of a cornea of the eye via one of the fsl laser or otherwise to provide access to the anterior chamber,
step 6 detaching the fsl from the conjunctiva,
step 7 separating such as by tearing the capsulorhexis of Im1 step 3,
step 8 (alternative to Im1 step 4) inserting an ultrasonic probe into the anterior chamber via the incision of step 5 and phacoemulsifying the crystalline lens,
step 9 flushing the debris from one of steps Im1 4 and 7 and Im1 7 and 8 from the eye via the at least first small incision of Im step 7,
step 10 (optional but preferred) instilling a viscoelastic into at least the capsule via the at least one opening of Im step 5,
step 11 inserting the prefolded disaccommodatively locked AIOL in accordance with the present invention into the capsule of the eye via the opening of step Im1 5,
step 12 aligning the haptics of the AIOL coincident with the minor diameter of the capsulorhexis of Im1 step 3,
step 13 flushing residual debris and foreign fluids from the eye (as appropriate) via the incision(s) of step 5,
step 14 closing the incision(s) of step 7 as appropriate and necessary,
step 15 preparation for discharge,
step 16: patient discharge, and
step 17: patient follow-up.

AIOL Implantation Method Two (Im2), Initial Anchoring of the AIOL by at Least One of Gluing and Mechanical Means:
Step 1 patient preparation,
step 2 removeably affixing an fsl laser to the conjunctiva of the eye,
step 3: fsl ablating a guide, such as a "tear on the dotted line" path, defining a conventional anterior capsule capsulorhexis into the anterior capsule (FIGS. 9B, 9C, leaderlines 9b.ac1, 9c.ac1),
step 4: fsl ablating a guide, such as a "tear on the dotted line" paths defining anterior capsule capsulorhexii for removing the portions of the anterior capsule unnecessary for initial anchoring and for shrinkwrap anchoring the AIOL (FIGS. 9B, 9C, leaderlines 9b.ac2a, 2b, 9bac3a, 3b),
step 5 fsl fragmenting of the cataractous or otherwise defective crystalline lens. (alternative to step 10),
step 6: cutting at least one small incision with the fsl laser or otherwise at the edge of the cornea to provide access to the anterior chamber,
step 7: detaching the fsl from the conjunctiva,
step 8: inserting a tensioning ring retained by an expander ring into the anterior chamber of the eye via the incision of Im2 step 6 and attaching the tensioning ring to the anterior capsule axisymmetrically and proximally to, and centrifugally with respect to the line of Im2 step 3 (tensioning ring attachment per published United States Patent Applications US20160000558A),
step 9: accessing the anterior capsule via Im2 step 7 and tearing loose the portion of the anterior capsule defined by Im2 step 3,
step 10 (alternative to Im1 step 5): inserting an ultrasonic probe into the anterior chamber via the opening of Im2 step 7 and phacoemulsifying the crystalline lens,
step 11: flushing the debris from steps Im1 9 and 5 or 9 and 10 from the eye,
step 12: inserting a disaccommodatively locked AIOL in accordance with the present invention into the capsule of the eye via the openings of Im2 steps 7 and 9,
step 13: aligning the haptics of the AIOL with a line of symmetry with respect to the "C" shaped capsuporhexii 9b.ac2a and 2b of Im2 step 4,
step 14: initial-anchoring the AIOL of step 10 to equatorial portions of the capsule intended to survive the capaulorhexis defined by Im1 step 4 via at least one of gluing the haptics of the AIOL to those portions and embedding the penetrators of AIOL haptics into those portions (See FIGS. 5, 6 and 7 and the descriptions thereof herein),
step 15: detaching and extracting the tensioning ring of Im2 step 8,
step 16: accessing the anterior capsule via step Im16 and tearing loose and extracting the portion of the anterior capsule defined by Im1 step 4 (including the tensioning ring of Im2 step 8 if still affixed thereto),
step 17: confirming initial anchoring via slack in the disaccommodative lock of the AIOL and if slack unlock the AIOL and if taut proceed to Im1 step 11,
step 18: flushing the residual debris from steps Im1 3 through 13 from the eye,
step 19: closing the incision of step 7 as appropriate and necessary,
step 20: preparing the patient for discharge,
step 21: patient discharge, and
step 22: patient follow-up.

Definition(s)

The term "biocompatible" refers to assemblies, subassemblies and components and the materials of which they are comprised that neither react adversely with one another when implanted in an eye nor adversely affect the eye and/or its components when implanted therein, and is, of course, intended to apply to the AIOLs of the present invention. Such materials include the acrylic and silicone polymers and the metals familiar from commercially available IOLs, from commercially available AIOLs such as Crystalens™ and SynchronyVu™, and the prior art such as that cited herein.

What is claimed is:

1. A method to replace a cataractous or otherwise defective crystalline lens to be surgically extracted from an eye with an accommodatively biased intraocular lens (AIOL) in accordance with the AIOL being folded, disaccommodatively locked, and contained within an injector for implantation in, and shrink-wrap anchoring and shrink-wrapped actuation by, a capsule of the eye of a patient, the capsule being surgically modified for the purpose; the AIOL comprising a bifurcated haptic AIOL, the haptic outboard portions of which further comprise at least one of flexible outriggers, gridded outriggers and gridded outboard portions; the method comprising the steps of:

applying anesthesia to the patient;
applying a speculum to the eye;
removeably affixing an fsl laser to a conjunctiva of the eye,
delineating, via a plurality of fsl cavitation burns, a guide on the anterior capsule capsulorhexis centered with respect to the optical axis of the eye and having a major diameter of 1.5-2 mm (millimeters) less than an equatorial diameter of the capsule and a minor diameter at least that of a disaccommodated distance between the outboard ends of the bifurcated portions of the haptics of the AIOL,
cutting at least a first small incision at an edge of a cornea of the eye via one of the fsl laser or otherwise to provide access to the anterior chamber,
one of (a) fsl cavitation cracking or otherwise preparing a cataractous or otherwise defective crystalline lens for extraction, and (b) inserting an ultrasonic probe into the anterior chamber via the incision and phacoemulsifying the crystalline lens,
detaching the fsl from the conjunctiva,
separating the capsulorhexis, from a portion of an anterior capsule outboard with respect thereto,
flushing debris from the eye,
inserting the prefolded disaccommodatively locked AIOL into the capsule of the eye via the incision,
aligning the haptics of the AIOL coincident with the minor diameter of the capsulorhexis,
flushing residual debris and foreign fluids from the eye as needed,
closing the incision(s) at the edge of the cornea as needed.

2. The method of claim 1, further comprising means for initially anchoring the AIOL to portions of at least the anterior capsule intended to survive capsulorexii by gluing, and wherein the means for initial anchoring by gluing comprises at least one glue retention groove in an outboard portion of each AIOL haptic, and wherein the at least one glue retention groove is filled with a biocompatible glue before AIOL implantation in the capsule.

3. The method of claim 1, further comprising, after the step of separating the capsulorhexis, instilling a viscoelastic into at least the capsule via the incision.

4. A method of replacing a cataractous or otherwise defective crystalline lens to be surgically extracted from an eye, the AIOL being folded, disaccommodatively locked, and contained within an injector for implantation in and shrink-wrap anchoring and shrink-wrapped actuation by a capsule of the eye, the capsule being surgically modified for the purpose, the AIOL comprising a bifurcated haptic AIOL, the haptic outboard portions of which further comprise a plurality of penetrators partially embedded into the haptic outboard portions for at least initially anchoring the AIOL to surviving portions of the surgically modified capsule and at least one of flexible outriggers, bending groove pivoted outriggers and bending groove pivoted gridded outriggers; the method comprising the steps of:

applying anesthesia to the patient;
applying a speculum to the eye;
removeably affixing an fsl laser to the conjunctiva of the eye,
delineating, via a plurality of anterior capsule fsl cavitation burns, a first guide defining a conventional anterior capsule capsulorhexis,
delineating via a plurality of anterior capsule fsl cavitation burns a second guide defining an anterior capsule capsulorhexis for removing the portions of the anterior capsule unnecessary for initial anchoring and for shrink-wrap anchoring of the AIOL by at least the anterior capsule,
performing one of ablating via the fsl laser at least one small opening at the edge of a cornea of the eye and manually cutting at least a first small incision at the edge of the cornea of the eye to provide access to the anterior chamber,
performing one of (a) fragmenting of the cataractous or otherwise defective crystalline lens via a plurality of fsl-induced ablative cracks, and (b) inserting an ultrasonic probe into the anterior chamber via the incision and phacoemulsifying the crystalline lens,
detaching the fsl from the conjunctiva,
inserting a tensioning ring retained by an expander ring into the anterior chamber of the eye via the incision of and attaching the tensioning ring to the anterior capsule axisymmetrically and proximally to and centrifugally with respect to the first guide,
accessing the anterior capsule via the at least first small incision, and separating the portions of the anterior capsule, defined by and contained within the second guide,
flushing debris from the eye,
inserting the accommodatively biased and disaccommodatively locked AIOL into the capsule of the eye via the incision,
aligning the haptics of the AIOL with respect to equatorial portions of the capsule,
anchoring the AIOL to equatorial portions of the capsule by embedding the penetrators of the AIOL haptics by applying appropriate pressure to one of an anterior lens ring and an anterior lens and releasing same,
detaching and extracting the tensioning ring,
accessing the anterior capsule and separating and extracting the remaining portions of the anterior capsule defined by the guides, including the tensioning ring if still affixed thereto,
confirming by visual inspection or otherwise initial anchoring of the AIOL via slack in the disaccommodative lock,
severing the disaccommodative lock if slack is confirmed,
flushing the residual debris and foreign fluids from the eye, and
closing the incision(s) at the edge of the cornea as needed.

5. The method of claim 4, further comprising means for initially anchoring the AIOL in the capsule by both gluing end penetrators, and wherein the means for initial anchoring by both gluing and penetrators comprises at least one glue retention groove flanked by at least one penetrator on each side thereof in an outboard portion of each AIOL haptic, and wherein the at least one glue retention groove is filled with a biocompatible glue before AIOL implantation in the capsule.

6. The method of claim 5, further comprising, after the step of separating the capsulorhexis, instilling a viscoelastic into at least the capsule via the incision.

\* \* \* \* \*